US00PP08036P

United States Patent [19]

Dehan

[11] Patent Number: Plant 8,036

[45] Date of Patent: Nov. 17, 1992

[54] IMPATIENS PLANT NAMED LAMBADA

[75] Inventor: Klara Dehan, Holon, Israel

[73] Assignee: Danziger - "Dan" Flower Farm, Post Beit Dagan, Israel

[21] Appl. No.: 730,608

[22] Filed: Jul. 16, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new cultivar of impatiens plant named Lambada characterized by its very large, intense red-purple flowers, dark green foliage which tends to red, elongated and spreading branching, and dark purple flower stems.

1 Drawing Sheet

The present invention relates to a new and distinctive cultivar of New Guinea Impatiens plant, botanically known as Impatiens and known by the cultivar name Lambada. The new cultivar was developed by me through controlled breeding by crossing a cultivar identified by breeding number 0-17-A as the seed parent with the cultivar identified as 174-11-A as the pollen parent.

Asexual reproduction of terminal or stem cuttings taken by applicant at Mishmar Hashiva, Israel has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Medium large foliage which extends well above the pot line.
2. Foliage is dark green tending to red.
3. Very large, intense red-purple flowers.
4. The contrast between the foliage color and flower color is very striking.
5. Elongated and spreading branching, making cultivar very adaptable to hanging pots.
6. Flower stems are dark purple.
7. The combined features of Lambada produce a very unique new cultivar.

The accompanying colored photograph is a top perspective view of a portion of a plant illustrating the foliage and flowers of Lambada with the colors being as true as it is reasonably possible to obtain in a colored reproduction of this type.

The following is a detailed description of my new impatiens cultivar based on plants produced under commercial practice in Mishmar Hashiva, Israel. The description was based on observations and measurements made in the winter and early spring.

Color references are made to The Royal Horticultural Society Colour Chart except where general terms of ordinary dictionary significance are used.

Parentage: 0-17-A × 174-11-A

Propagation:

A. *Type cutting.*—Leaf cuttings with axillary buds and without flower buds.

B. *Time to initiate roots.*—8–10 days both at 25°–30° C. summer, and 20°–22° C. winter.

C. *Rooting habit.*—Good.

Plant description:

A. *Form.*—Medium size, mounded.

B. *Habit of growth.*—Vigorous with good branching; the branches are elongated and spreading, making Lambada suitable for hanging pots.

C. *Foliage desription.*—Very dark foliage and medium large leaves. (1) Size: 9–9.5 cm in length and 3.0–3.5 cm wide. (2) Shape: Oval. (3) Margin: Serrated. (4) Color: Young foliage on top side, darker than 147A; under side 187B. Mature foliage top side slightly darker than 147A; under side 187A. (5) Venation: 187A.

Flowering description:

A. *Flowering habits.*—Very floriferous, with five days required from bud to open flower.

B. *Natural flowering season.*—Natural flowering season in moderate climate is in the spring, and continuing until frost. In Israel flowering also occurs in the winter.

C. *Flower bud description.*—Normal.

D. *Flowers borne.*—Every branch has approximately 5–6 buds at the top of every branch. It takes about two to three weeks until all the flowers are opened and in the same time there are two-three flowers on each branch.

E. *Quantity of flowers.*—Very floriferous; flowers are open on every branch, with the quantity of flowers being about 30–40 open flowers at the same time. Flowering is continuous at temperatures above approximately 10° C. and with minimum levels of light.

F. *Petals.*—(1) Shape: Two pairs of petals are heart shaped, and the fifth is larger and non-heart shaped. (2) Color: Top side in winter when opening is closet to red-purple 57A, but tending, somewhat more to red; no fading. Underside 58B. (3) Number of petals: Five. (4) Size of flowers: Very large, 6.5–7.0 cm in diameter.

G. *Reproductive organs.*—(1) Stamens: One in number. (a) Anther color: White and purple. (b) Pollen color: White. (2) Pistils: (a) Stigma: Cone shape, dark purple in color. (b) Style: Green in color. (c) Ovaries: One in number, size 1.5 mm, green in color.

I claim:

1. A new and distinct cultivar of impatiens plant named Lambada, as illustrated and described.

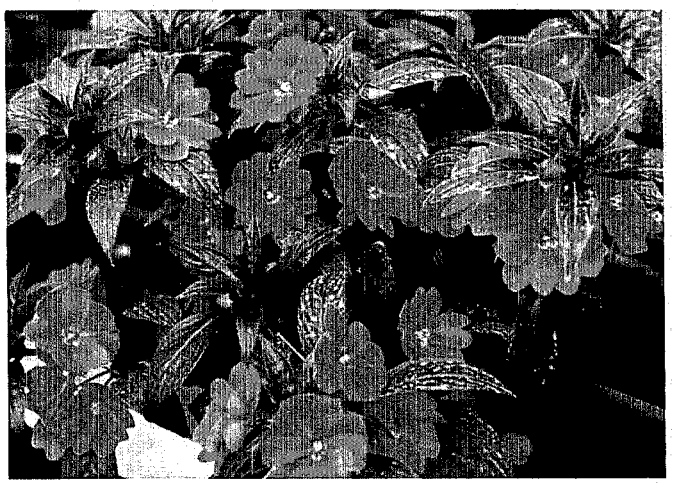

* * * * *